United States Patent
Bonfiglio

(10) Patent No.: US 8,496,914 B2
(45) Date of Patent: Jul. 30, 2013

(54) ANTIBACTERIAL ORAL RINSE FORMULATION FOR PREVENTING CORONARY ARTERY DISEASE

(76) Inventor: Richard Paul Bonfiglio, Murrysville, PA (US)

( * ) Notice: Subject to any disclaimer, the term of this patent is extended or adjusted under 35 U.S.C. 154(b) by 1173 days.

(21) Appl. No.: 11/638,681

(22) Filed: Dec. 13, 2006

(65) Prior Publication Data

US 2007/0154414 A1 Jul. 5, 2007

Related U.S. Application Data

(60) Provisional application No. 60/749,928, filed on Dec. 13, 2005, provisional application No. 60/773,356, filed on Feb. 14, 2006.

(51) Int. Cl.
| | | |
|---|---|---|
| *A61Q 11/00* | (2006.01) | |
| *A61K 8/02* | (2006.01) | |
| *A61K 36/61* | (2006.01) | |
| *A61K 36/53* | (2006.01) | |
| *A61K 36/534* | (2006.01) | |
| *A61K 36/752* | (2006.01) | |

(52) U.S. Cl.
USPC ............... 424/49; 424/58; 514/729; 514/736; 514/747; 514/901

(58) Field of Classification Search
USPC ............... 424/49, 58; 514/729, 736, 747, 901
See application file for complete search history.

(56) References Cited

U.S. PATENT DOCUMENTS

| | | | |
|---|---|---|---|
| 4,975,285 A | 12/1990 | Ratcliff | |
| 6,814,958 B1 * | 11/2004 | Sekimoto | 424/58 |
| 2002/0109123 A1 | 8/2002 | Woosley | |
| 2003/0103914 A1 | 6/2003 | Lawlor | |
| 2004/0265247 A1 | 12/2004 | Abiru et al. | |
| 2005/0169852 A1 | 8/2005 | Roberge et al. | |
| 2005/0271602 A1 * | 12/2005 | Milanovich et al. | 424/49 |
| 2008/0031831 A1 * | 2/2008 | Laali | 424/58 |

OTHER PUBLICATIONS

William Joel Meggs, M.D., Ph.D., Carol Sveg, "The Inflammation Cure", 2004, published by McGraw-Hill Professional.*
Vicki Pitman, "Aromatherapy: A Practial Approach", 2004, published by Nelson Thornes.*
Vergis et al., "Topical antibiotic prophylaxis for bacteremia after dental extractions", Oral Surgery, Oral Medicine, Oral Pathology, Feb. 2001, vol. 91, pp. 162-166.*
Nutrimart.com, Green Tea Extract, p. 1, retrieved Dec. 19, 2011.*

* cited by examiner

*Primary Examiner* — Lezah Roberts
(74) *Attorney, Agent, or Firm* — Acker Wood IP Law, LLC; Gwen R. Acker Wood

(57) ABSTRACT

The present invention provides an antibacterial oral rinse formulation having enhanced antibacterial activity against oral bacteria associated with infectious and inflammatory processes for preventing and/or treating inflammatory diseases or inflammatory processes associated with diseases in an individual by inhibiting the transient bacteremia associated with oral hygiene activities by the individual. Also provided is a method for preventing and/or treating inflammatory diseases or inflammatory processes associated with diseases in an individual by inhibiting transient bacteremia associated with oral hygiene activities by the individual, comprising rinsing with the antibacterial oral rinse formulation for a period of time immediately prior to engaging in oral hygiene activities.

13 Claims, No Drawings

ANTIBACTERIAL ORAL RINSE FORMULATION FOR PREVENTING CORONARY ARTERY DISEASE

The present invention claims priority to U.S. Provisional Application No. 60/749,928, filed Dec. 13, 2005 and to U.S. Provisional Application No. 60/773,356, filed Feb. 14, 2006, both of which are incorporated herein by reference.

BACKGROUND OF THE INVENTION

1. Field of the Invention

The present invention relates to oral mouth rinse formulations and, more particularly, to antibacterial oral mouth rinse formulations having enhanced antibacterial activity against oral bacteria associated with infectious and inflammatory processes involved in atherosclerotic plaque formation and coronary artery disease.

2. Description of Related Art

Atherosclerosis is the leading cause of death and disability in the developed world. Coronary artery disease is caused by atherosclerosis, which is a narrowing of the coronary arteries due to fatty build-up of plaque. The conventional risk factors for atherosclerosis have long been known, such as dyslipidemia, hypertension, smoking, diabetes and family history. These risk factors, however, fail to account for approximately 50% to 70% of atherosclerotic events in the general population. Many other putative risk factors for atherosclerosis have been proposed, including traits related to obesity, inflammation and infection.

Periodontal disease is a candidate risk factor for atherosclerosis that shares many of these related traits. The periodontal diseases reflect a spectrum of oral pathology from gingivitis (gum inflammation) to severe periodontitis (progressive loss of gum attachment) with alveolar bone and tooth loss.

The pathogenesis of periodontal disease is thought to be due to accumulation of dental plaque (bacteria in subgingival biofilms) with consequent mucosal infection and inflammation. Abnormal host responses, with upregulation of matrix metalloproteinases, contribute to a more rapid disease progression in some patients. Periodontal disease is more common with cigarette smoking, obesity and diabetes, and it affects about 75% of the adult population in the United States, with about 20% to 30% of adults having severe forms (Al-Zahrani, M.S. et al., J. Periodontol., 74:610-615, 2003). Lack of oral hygiene is recognized as a cause of dental caries, plaque formation and periodontitis. Additionally, lack of oral hygiene can result in systemic effects, including a decline in general health, impairment of the immune system and increased respiratory infections.

Increasing evidence over the past decade suggests a link between periodontal disease and atherosclerosis. Indeed, oral bacteria have been cultured in coronary artery plaques and thus are believed to contribute to the progression of coronary artery disease by increasing inflammation and immune system components of inflammation.

Multiple cross-sectional studies have demonstrated a higher incidence of atherosclerotic complications in patients with periodontal disease, and severe periodontal disease has been shown to be associated with an almost four-fold higher incidence of myocardial infarction compared to patients without periodontal disease (Arbes, S. J., Jr. et al., J. Dent. Res., 78:1777-1782, 1999). Cross-sectional studies also have shown that cardiovascular risk associated with periodontal disease is dependent on the severity of the periodontal disease and independent of the aforementioned conventional risk factors (Armitage, G. C., Oral Disease, 6:335-350, 2000). For example, several case-control studies have indicated that subgingival periodontal pathogenic infection may be associated with myocardial infarction (Genco, R. et al., J. Amer. Dent. Assoc., 133 Suppl:14S-22S, 2002).

Additionally, several prospective longitudinal studies have demonstrated a 1.5 to 2.5-fold increased risk of developing complications of atherosclerosis among patients with periodontal disease (Morrison, H. I. et al., J. Cardiovasc. Risk, 6:7-11, 1999; Wu, T. et al., Arch. Int. Med., 160:2749-2755, 2000). Other studies have shown a thrombogenic role for the oral bacteria *Streptococcus sanguis*, contributing to the development of the vegetative lesion in infective endocarditis and a thrombotic mechanism to explain the additional contributed risk of periodontitis to myocardial infarction (Herzberg, M. C. et al., J. Periodontol., 67(S10):1138-1142, 1996).

The presence of periodontal infection is believed to lead to brief episodes of bacteremia with inoculation of atherosclerotic plaques by periodontal pathogens such as *Porphyroinonas gingivalis*, *Actinobacillus actinomycetemcomitans* and *Bacteroides forsythus*. Subsequent growth of these bacteria then may cause inflammation and atherosclerotic plaque instability. Indeed, there is evidence, using immunostaining and polymerase chain reaction for bacterial rDNA, that these pathogens are present in 18% to 30% of carotid atheromas (Haraszthy, V. I. et al., J. Periodontol., 71:1554-1560, 2000).

Common oral bacteria that contribute to dental caries, periodontitis and transient bacteremia include the following: *Streptococcus mutans*, a gram-positive bacterium and the primary etiological agent of dental caries, which possesses several virulence factors that allow it to accumulate within the dental biofilm and produce and tolerate acids which cause caries lesions; *Porphyromonas gingivalis*, a gram-negative, anaerobic pathogenic oral bacterium, which is a major etiological agent in the initiation and progression of severe forms of periodontal disease. Infection with *P. gingivalis* may predispose an individual to more serious systemic conditions, such as cardiovascular disease and to delivery of preterm infants; *Treponema denticola*, an obligate anaerobic bacterium found in the oral cavity of humans and typically associated with periodontal disease. *T. denticola* DNA and antigens have been detected in atherosclerotic lesions of the aorta in human patients. *T. denticola* infection of expectant mothers also may cause delivery of preterm infants; *Fusobacterium nucleatum*, an anaerobic gram-negative oral bacterium found in the normal flora of the mouth, which has been shown to play a role in periodontal disease. Although *F. nucleatum* is not considered a major dental pathogen on its own, it can adhere to a wide range of other plaque organisms, such as *P. gingivalis*, and contribute to the development of periodontitis as well as invasive human infections of the head and neck, chest, lung, liver and abdomen; *Prevotella intermedia*, a bacterium that forms an association complex with other oral bacteria and which virulence factors have been identified, such as hemagglutinating, hemolytic and hemoglobin-binding activities. Clinical isolates of *P. intermedia* have shown resistance to antibiotics, and thus this bacterium may be one of the more drug-resistant periodontal pathogens; and *Actinobacillus actinomycetemcomitans*, a facultative oral anaerobic bacterium, which has been shown to be strongly associated with localized juvenile periodontitis.

Improved oral hygiene has lead to a substantial decrease in the incidence of dental caries and periodontal disease over the last half century. During the same time period, however, the incidence and prevalence of atherosclerosis, coronary artery disease and associated myocardial infarction has increased markedly. Interestingly, live oral bacteria have been detected in coronary artery plaques.

Bacteremia has long been known to occur during dental treatment, such as tooth extractions, gum procedures and even tooth cleaning. Indeed, individuals at risk for valvular vegetations, including those individuals with mitral valve prolapse, routinely receive prophylactic antibiotics before dental treatment.

Bacteremia also is known to occur following oral hygiene activities, such as tooth brushing and flossing. Because such bacteremia has been assumed to be transient and inconsequential, no prophylaxis or treatment typically has been recommended for these activities. However, bacteremia associated with oral bacteria may result in inflammatory processes in various regions and systems of the body such as the circulatory system, contributing to diseases of the affected organs or body sites. For example, daily transient bacteremia caused by liberation of oral bacteria from the oral cavity into the circulation may contribute to inflammatory processes associated with autoimmune disorders and other disorders/diseases, such as rheumatoid arthritis, multiple sclerosis and Alzheimer's disease.

Additionally, it is known that individuals with poor oral hygiene, i.e., individuals that only occasionally brush their teeth and rarely tooth floss, and thus have an increased bacterial load in the oral cavity, have an increased risk for coronary artery disease. This may be due, in part, to the transient bacteremia that occurs when the individual does brush and/or floss, which bacteria in the circulation inoculates atherosclerotic plaques.

It also is known that poorly-controlled diabetic individuals have an increased risk for coronary artery disease. This may be due, in part, to the increased glucose levels present in the body fluids of the diabetic individuals, such as saliva. The increased bacterial load in the saliva of diabetics contributes to excessive growth of oral bacteria, which leads to transient bacteremia subsequent to tooth brushing and/or flossing.

There exists a need, therefore, to inhibit the transient bacteremia associated with routine oral hygiene activities of tooth brushing and tooth flossing, which bacteremia may be a significant risk factor for atherosclerosis and associated coronary artery disease, myocardial infarction and death, as well as other inflammatory processes, disorders and diseases in the body.

SUMMARY OF THE INVENTION

The present invention fulfills this need by providing an antibacterial oral rinse formulation for preventing and/or treating inflammatory diseases or inflammatory processes associated with diseases in an individual by inhibiting the transient bacteremia associated with oral hygiene activities by the individual.

The present invention also provides a method for preventing and/or treating inflammatory diseases or inflammatory processes associated with diseases in an individual by inhibiting transient bacteremia associated with oral hygiene activities by the individual, comprising rinsing with the antibacterial oral rinse formulation for a period of time immediately prior to engaging in the oral hygiene activities.

The present invention further provides a method of inhibiting bacterial growth on an oral hygiene device, comprised of storing the oral hygiene device in a suitable receptacle filled with the antibacterial oral rinse formulation between usage of the oral hygiene device.

DETAILED DESCRIPTION OF THE INVENTION

One aspect of the present invention provides an antibacterial oral rinse formulation for preventing and/or treating inflammatory diseases or inflammatory processes associated with diseases in an individual by inhibiting the transient bacteremia associated with oral hygiene activities by the individual.

The antibacterial oral rinse formulation is comprised of at least three or more of the following active ingredients: bioflavonoids, which include, without limitation, polyphenols, such as gallic acid and catechin and their derivatives theogallin, gallocatechin, epigallocatechin, epicatechin or epigallocatechin gallate; essential oils, which include, without limitation, terpene hydrocarbons, such as alpha-pinene, beta-pinene, p-cymene, limonene, aromadendrene, 1,8-cineole, terpinolene, alpha-terpineol, alpha-terpinene, gamma-terpinene, terpinen-4-ol, alloocimene, delta-3-carene, dertol, dertosol or dipentene; oxygenated terpenes, which include, without limitation, terpinen-5-ol; *Lavandula officinalis; Citrus limon; Commiphora pyrrha; Pogostemon patchouli; Mentha piperita; Rosemarinus officinalis; Eucalyptus globules* or *Mentha arvensis*; quaternary ammonium compounds, which include, without limitation, cetylpyridium chloride; bis-phenols, which include, without limitation, triclosan; and bigualides, which include, without limitation, chlorhexidine.

In an embodiment, the antibacterial oral rinse formulation is comprised of the following active ingredients: green tea extract, which contains bioflavonoid polyphenols, in which the following ingredients are contained in the bioflavonoid polyphenols: gallocatechin, epigallocatechin, epicatechin and epigallocatechin gallate in an amount of between about 5 to 50% w/v, preferably between about 10 to 30% w/v; most preferably between about 15 to 20% w/v; tea tree oil, which contains beta-pinene, p-cymene, limonene, aromadendrene, 1,8-cineole, terpinolene, alpha-terpineol and terpinen-4-ol in an amount of between about 0.5 to 25% v/v, preferably between about 1 to 5% v/v, most preferably between about 2 to 3% v/v; and mint oil (*Mentha arvensis*) in an amount of between about 0.1 to 5% v/v, preferably between about 0.2 to 2% v/v, most preferably between about 0.5 to 1% v/v.

Any suitable green tea may be used in the formulation of the present invention. Green tea, as well as all other teas, is derived from the same plant, *Camellia sinensis*, an evergreen shrub native to eastern Asia. The difference in the teas is due to how they are prepared. Different methods of curing the leaves create different tea products. Green tea is prepared from the steamed and dried leaves of the shrub. Black tea is produced by withering, rolling, fermenting and then drying the leaves. Oolong tea is semi-fermented and considered an intermediate product between green and black tea.

The most abundant components of green tea are polyphenols, such as gallic acid and catechin, and their derivatives theogallin, gallocatechin, epicatechin and epigallocatechin gallate. The fresh leaves contain about 3% to 4% caffeine, about 0.15% to 0.2% theobromine, about 0.02% to 0.04% theophylline and other methylxanthines. With fermentation, the catechins partially change into oligomeric quinines, including theaflavine, theaflavine acid and thearubigene, or to the non-water-soluble flavonoids such as quercetin, kaempferol and myrecetin. Green tea also contains B vitamins and ascorbic acid, which are destroyed in the process of making black tea. The essential oil contains more than three hundered components including aldehydes, phenylethyl alcohols, phenols, hexenal, hexenol, linalool, dihydroactinidiolide and p-vinylphenol.

Possible pharmacologic actions of green tea include effects on lipid metabolism; antimicrobial, antioxidant and antimutagenic effects; and a wide variety of anticancer actions.

Any suitable tea tree oil may be used in the antibacterial oral rinse formulation of the present invention. Tea tree oil is a volatile essential oil derived from the leaves of the tea tree (*Melaleuca alternifolia*), which is a member of the family *Myrtaceae* and is one of over 150 species of *Melaleuca*, indigenous to Australia. The tea tree grows in swampy, lowlying areas on the northern coast of New South Wales. Less commonly, tea tree oil is extracted from *M. linarifolia* and *M. dissitiflora*.

Tea tree oil extraction from the leaves of *M. alternifolia* typically is performed by steam-distillation. The leaves contain about 2% of a pale-yellow volatile oil. Tea tree oil is a complex mixture of terpenes and related alcohols with over one hundred components. Up to 90% of the whole oil content of tea tree oil is made up of the following components: terpinen-4-ol, 1,8-cineole, alpha-terpineol, terpinolene and alpha and gamma-terpinene. International standards of tea tree oil have been most recently defined by ISO 4730 (International Organization for Standardization, 1996, International Standard ISO 4730 of Melaleuca, terpinen-4-ol type Tea tree oil, ISO, Geneva). The main antimicrobial component in tea tree oil is terpinen-4-ol.

Any suitable mint oil may be used in the formulation of the present invention. Mint oil is steam distilled from the flowering tops of Japanese mint, a perennial aromatic herb native to Japan, now cultivated in subtropical climates around the world. Mint oil consists of volatile oil obtained from *Mentha arvensis*.

Additionally, the antibacterial oral rinse formulation of the present invention contains inactive ingredients, which include, without limitation, preservatives, solubilizers, neutralizers, flavorings, colorings and the like. These ingredients, where present, are incorporated in the formulation in amounts which do not adversely affect the properties and characteristics of the formulation.

In particular, the antibacterial oral rinse formulation of the present invention is comprised of the following inactive ingredients: preservatives, which include, without limitation, sodium sorbate, potassium sorbate, calcium sorbate, benzoic acid, sodium benzoate, potassium benzoate, calcium benzoate, propylparaben, methylparaben, dimethyl dicarbonate, sodium propionate, calcium propionate, potassium propionate and calcium disodium ethylenediaminetetraacetate; emulsifiers, which include, without limitation, lecithin, sodium citrates, sodium phosphates, potassium phosphates, calcium phosphates, polyethylene and polysorbate 80; coloring agents, which include, without limitation, tartrazine, chlorophyll, caramel, carotene, annatto extracts, lycopene, lutein, saffron, anthocyanins, calcium carbonate, titanium dioxide, tannic acid, erythrosine, amaranth, carmines, curcumin and riboflavin; sweeteners, which include, without limitation, sorbitol, mannitol, aspartame, isomalt, saccharin, sucralose, alitame, maltitol, lactitol, xylitol and erythritol; humectants, which include, without limitation, glycerin, polydextrose, propylene glycol, sodium lactate and potassium lactate; flavorings, which include, without limitation, spearmint, peppermint and other mint flavorings; and buffering agents, which include, without limitation, acetic acid, lactic acid, sodium lactate, potassium lactate, calcium lactate, citric acid, tartaric acid, sodium phosphates, sodium biphosphates, potassium phosphates, calcium phosphates, magnesium phosphates, adipic acid, succinic acid, sodium fumarate, potassium fumarate, calcium fumarate, sodium carbonate, potassium carbonate and water.

In an embodiment, the antibacterial oral rinse formulation is comprised of the following inactive ingredients: the preservative calcium disodium ehtylenediaminetetraacetate, the emulsifier polysorbate 80, the coloring agents chlorophyll and carotene, the sweetener aspartame, the humectant glycerin, the buffering agents sodium biphosphate and sodium phosphate and water.

Another aspect of the present invention provides a method for preventing and/or treating inflammatory diseases or inflammatory processes associated with diseases in an individual by inhibiting transient bacteremia associated with oral hygiene activities by the individual, comprising rinsing with the antibacterial oral rinse formulation for a period of time immediately prior to engaging in the oral hygiene activities. Preferably, the antibacterial oral rinse formulation is in contact with the oral cavity of an individual for a time ranging between about 1 second to about 5 minutes, more preferably for about 10 seconds to 3 minutes, and most preferably for about 30 to 60 seconds. The amount of the antibacterial oral rinse formulation contacted with the oral cavity of an individual ranges from between about 0.1 liquid ounce to about 10.0 liquid ounces, preferably about 1 liquid ounce.

Typical oral hygiene activities include, without limitation, tooth brushing and tooth flossing.

A further aspect of the present invention provides a method of inhibiting bacterial growth on an oral hygiene device, comprised of storing the oral hygiene device in a suitable receptacle filled with the antibacterial oral rinse formulation between usage of the oral hygiene device.

Suitable oral hygiene devices include, without limitation, manual or electrically-operated toothbrushes and dental flosses.

Inflammatory diseases and inflammatory processes associated with disease which may be prevented and/or ameliorated with the antibacterial oral rinse formulation of the present invention include, for example and without limitation, atherosclerotic plaque formation in coronary arteries, rheumatoid arthritis, lupus erythematosus and related disorders, osteoarthritis, inflammatory bowel disease, thyroiditis, chronic obstructive pulmonary disease, pericarditis, asthma, chronic fatigue syndrome, gout, kawasaki's disease, lymphadenopathy, polymyalgia rheumatica, psoriasis, raynaud's phenomenon, sarcoidosis, sjogren's syndrome, spondyloarthropathies or vasculitides.

The antibacterial oral rinse formulation of the present invention is efficacious especially for individuals suffering from diabetes mellitus, who are at an increased risk for cardiovascular disease. It is known that diabetic individuals have a two- to three-fold increased risk for coronary artery disease and have two- to four-fold higher coronary artery disease morbidity and mortality rates because of the increased glucose load present in their body fluids, such as saliva. If blood glucose levels are higher than normal and are not controlled, this can affect the lining of the body's arterial walls, which may increase susceptibility to the formation of atherosclerosis. The increased risk for coronary artery disease also may be due, in part, to increased glucose levels present in saliva of poorly-controlled diabetics. It is believed, without being bound by the theory, that increased glucose levels in saliva contribute to excessive growth of oral bacteria in the oral cavity, resulting in transient bacteremia subsequent to tooth brushing or flossing and concomitant growth of oral bacteria in coronary arteries. Therefore, by inhibiting oral bacterial growth in the oral cavity of diabetic individuals, this can substantially prevent inoculation of the coronary arteries with oral bacteria in these individuals.

Similarly, individuals with poor oral hygiene who only occasionally brush their teeth and rarely floss their teeth also have an increased risk of coronary artery disease. This may be due, in part, to the increased bacterial load present in the oral cavity because of their poor hygiene, resulting in transient bacteremia when they do tooth brush and/or floss, leading to subsequent growth of oral bacteria in the coronary arteries.

The present invention is more particularly described in the following non-limiting examples, which are intended to be illustrative only, as numerous modifications and variations therein will be apparent to those skilled in the art.

EXAMPLES

Example 1

In Vitro Antimicrobial Action of the Antibacterial Oral Rinse Formulation Comprised of Green Tea Extract, Tea Tree Oil and Mint This study investigates the in vitro activity of the antibacterial oral rinse formulation of the present invention comprised of the active ingredients green tea extract, tea tree oil and mint oil.

The green tea extract contains the bioflavonoid polyphenols gallocatechin, epigallocatechin, epicatechin and epigallocatechin gallate in equal amounts, in which the total amount of green tea extract in the antibacterial oral rinse formulation is present in an amount of 20% w/v.

The tea tree oil contains 75% v/v terpinen-4-ol; 5% v/v beta-pinene; 2.0% v/v p-cymene; 2.0% v/v limonene; 2.0% v/v aromadendrene; 2.0% v/v 1,8-cineole; 2.0% v/v terpinolene; and 2.0% v/v alpha-terpineol, in which the total amount of tea tree oil in the antibacterial oral rinse formulation is 3% v/v.

The mint oil (Mentha arvensis) is present in the antibacterial oral rinse formulation in an amount of 1% v/v.

In addition, the following inactive ingredients are contained in the antibacterial oral rinse formulation: calcium disodium ehtylenediaminetetraacetate, polysorbate 80, chlorophyll, aspartame, glycerin, sodium biphosphate and water.

The antimicrobial effectiveness of the antibacterial oral rinse formulation is determined in terms of minimum inhibitory concentration (MIC), minimum bactericidal concentration (MBC) or minimum fungicidal concentration (MFC).

The isolates of microorganisms that are assayed include the following six oral bacterial isolates: *Streptococcus mutans, Porphyromons gingivalis, Treponema denticola, Fusobacterium nucleatum, Prevotella intermedia* and *Actinobacillus actinomycetemcomitans*.

An agar dilution assay is used to determine the MICs of the antibacterial oral rinse formulation. It is expected that the MICs of the antibacterial oral rinse formulation in all of the bacterial isolates will be between about 0.1-4.0% (v/v). Additionally, an investigation regarding how quickly the cells of the oral bacteria isolates are destroyed is performed. It is expected that treatment with the antibacterial oral rinse formulation will result in a greater than 3 log decrease in viable cells after approximately 30 seconds treatment and that after approximately one minute a substantial percentage of bacteria as well as other microorganisms, will be destroyed.

This study will show that that antibacterial oral rinse formulation exerts a relatively rapid killing effect on oral bacteria and other microorganisms.

Example 2

In Vivo Antimicrobial Action of the Antibacterial Oral Rinse Formulation Comprised of Green Tea Extract, Tea Tree Oil and Mint Oil This study investigates the in vivo activity of the antibacterial oral rinse formulation of the present invention comprised of green tea extract, tea tree oil and mint oil.

Materials and Methods
Antibacterial Oral Rinse Formulation

This formulation consists of the active ingredients green tea extract, tea tree oil and mint oil.

The green tea extract contains the bioflavonoid polyphenols gallocatechin, epigallocatechin, epicatechin and epigallocatechin gallate in equal amounts, in which the total amount of green tea extract in the antibacterial oral rinse formulation is present in an amount of 20% w/v.

The tea tree oil contains 75% v/v terpinen-4-ol; 5% v/v beta-pinene; 2.0% v/v p-cymene; 2.0% v/v limonene; 2.0% v/v aromadendrene; 2.0% v/v 1,8-cineole; 2.0% v/v terpinolene; and 2.0% v/v alpha-terpineol, in which the total amount of tea tree oil in the antibacterial oral rinse formulation is 3% v/v.

The mint oil (Mentha arvensis) is present in the antibacterial oral rinse formulation in an amount of 1% v/v.

In addition, the following inactive ingredients are contained in the antibacterial oral rinse formulation: calcium disodium ehtylenediaminetetraacetate, polysorbate 80, chlorophyll, aspartame, glycerin, sodium biphosphate and water.

Groups

Two groups of individuals, an experimental group and a control group, consisting of 16 healthy individuals in each group, are used in this study. The groups are matched for sex and age.

The subjects in the experimental group will gargle with one liquid ounce of the antibacterial oral rinse formulation, kept at 26° C., for one minute immediately prior to brushing their teeth with an electrically-operated toothbrush for two minutes.

The subjects in the control group will gargle with one liquid ounce of distilled water, kept at 26° C., for one minute immediately prior to brushing their teeth with an electrically-operated toothbrush for two minutes.

Blood Culture Assay

The isolates of microorganisms that are cultured are the following six oral bacterial isolates: *Streptococcus mutans, Porphyromons gingivalis, Treponema denticola, Fusobacterium nucleatum, Prevotella intermedia* and *Actinobacillus actinomycetemcomitans*.

To test for the presence of the above-described oral bacterial isolates in the bloodstream of the 16 subjects, a blood culture assay is performed. Such blood culture assays are routinely done by those skilled in the art and protocols for their performance are well known by those skilled in the art. Briefly, a sample of blood is collected and placed in a container with substances that promote the growth of bacteria. The type of bacteria that grows is identified by chemical tests and by examining the culture under a microscope. To increase the chances of identifying bacteria in the blood, two or three blood samples from different veins of a subject are usually taken. If no bacteria grow, the blood culture is deemed negative.

Results

The results will show that the blood samples from the subjects in the experimental group were negative for all six bacterial isolates. In contrast, the blood samples from the subjects in the control group will all show the presence of at least one of the six bacterial isolates.

Discussion

Green tea is known to have antibacterial effects against oral bacteria and several pathogenic strains common in the gastrointestinal tract. In particular, green tea extracts are known to be bactericidal against the growth of diarrhea-causing *Staphylococcus aureus, Staphylococcus epidermidis, Vibrio parahaemolyticus, Campylobacter jejuni* and *Vibrio cholerae*. Green tea extracts also are known to be effective against pathogenic methicillin-resistant *S. aureus* and, to some extent, against penicillin-resistant *S. aureus* (Yam, T. S. et al., J. Antimicrob., Chemother., 42(2):211-216, 1998).

Additionally, green tea polyphenols are known to completely inhibit the growth and adherence of the oral bacterium *Porphyromonas gingivalis* in a concentration of 250-500 pg/ml (Sakanaka, S. et al., Biosci. Biotechnol. Biochem., 60(5):745-749, 1996), and a 1.0 mg/ml of a green tea polyphenol solution has been shown to inhibit the proliferation of the oral bacterium *Streptococcus mutans* (Saeki, Y. et al., Bull., Tokyo Dent., Coll., 34(1):33-37, 1993).

Green tea also has been administered in cases of hepatitis, for protection of the liver against chemical toxins and topically in various skin disorders. For example, psoriasis and a number of other common skin diseases typically are treated with psoralens combined with exposure to ultraviolet A (PUVA). Although this treatment combination is highly effective, careful follow-up studies have shown that this treatment greatly increases the risk for developing cutaneous squamous cell carcinoma and melanoma (Zhao, J. F. et al., J. Invest. Dermatol., 113(6):1070-1075, 1999). Green tea and its constituent polyphenols have been shown to protect against ultraviolet B-induced carcinogenesis and reduce the growth rate of established tumors in the skin. Zhao and coworkers showed that pre- and post-treatment with standardized green tea extract abrogated the PUVA-induced photochemical damage to skin.

Tea tree oil is known to have antibacterial action. For example, tea tree oil is known to inhibit several common skin pathogens. Terpinen-4-ol and whole tea tree oil have been shown to be equally effective for activity against *Staphylococcus aureus* (Williams, L. et al., Aust. J. Pharmacy, 78:285-287, 1997). Additionally, three major components of tea tree oil, namely, terpinen-4-ol, alpha-terpineol and alpha-pinene, have been shown to inhibit three bacterial strains: *Staphylococcus aureus, Staphylococcus epidermidis* and *Propionibacterium acnes* (Raman A. et al., Lett. Application Microbiol., 21(4)242-245, 1995).

Mint oil is known to be effective for treating indigestion, nausea, sore throat, diarrhea, colds, and headaches.

Studies of both atherosclerotic plaque and circulating vascular elements have provided ample and growing evidence for an inflammatory process in atherothrombosis/thrombosis (see, e.g., Ross, R., NEJM, 340:115-126, 1999). Histologic studies have shown accumulation of activated inflammatory cells, such as macrophages, T lymphocytes and mast cells, in atherothrombotic plaque, especially unstable and disrupted plaques. Additionally, increases in circulating markers of inflammation, for example C-reactive protein and interleukins, have been demonstrated. The specific triggers for the vascular inflammatory responses observed in atherothrombosis are uncertain. However, infectious as well as non-infectious stimuli are believed to be involved.

It is well known that infection is the classic stimulus for inflammation, which is directed at eradication or containment of the offending organism. Infection as an inflammatory stimulus of chronic diseases, such as, for example and without limitation, atherosclerosis or rheumatoid arthritis, has now been recognized (see, e.g., Shah, P. K., Cardiol. Clin., 17:271-281, 2000).

The human mouth provides a habitat for a diverse range of bacteria, viruses, protozoa and fungi. These microorganisms colonize every surface in the mouth, including the cheeks, tongue, palate and teeth. Additionally, the variety of microorganisms is different for each individual, with each individual having a stable load of microorganisms that can be altered by factors such as disease, drug use, hygienic activities, aging, etc.

For example, the bacterial flora in gingival lesions are known to produce a complex biofilm that forms a prominent layer in the oral cavity. The bacterial flora cohabitating in the biofilm consist of a variety of bacterial strains, some of which are benign and others of which are important with respect to contributing to coronary artery disease. However, it is believed, without being bound by the theory, that there is a deleterious synergistic effect of having a multiplicity of strains of oral bacteria cohabitating in a particular biofilm, in which the synergistic effect may increase the overall deleterious effect of the biofilm, and thus may increase the adverse effect of each strain of oral bacteria with respect to the initiation or exacerbation of coronary artery disease.

It will be appreciated by those skilled in the art that changes could be made to the embodiments described above without departing from the broad inventive concept thereof. It is understood, therefore, that this invention is not limited to the particular embodiments disclosed, but it is intended to cover modifications that are within the spirit and scope of the invention, as defined by the appended claims.

The invention claimed is:

1. An antibacterial oral rinse formulation for inhibiting transient bacteremia associated with causing inflammatory diseases or inflammatory processes associated with diseases as a result of oral hygiene activities in an individual, consisting essentially of the following compounds from tea tree oil: 75% v/v terpinen-4-ol, 2% v/v 1,8-cineole, 2% v/v alpha-terpineol, 5% v/v beta-pinene, 2% v/v p-cymene, 2% v/v limonene, 2% v/v aromadendrene, and 2% v/v terpinolene, in which the total amount of the compounds from tea tree oil in the formulation is 3% v/v; the following compounds from green tea extract in equal amounts: gallocatechin, epigallocatechin, epicatechin, and epigallocatechin gallate, in which the total amount of the compounds in the green tea extract in the formulation is 20% v/v; *Menthas arvensis*, in which the total amount of the *Menthas arvensis* in the formulation is 1% v/v; chlorophyll; calcium sorbate; polysorbate 80; glycerin; sodium biphosphate; and water, wherein the antibacterial oral rinse formulation is contacted with an individual's oral cavity for a period of time immediately prior to said oral hygiene activity.

2. The antibacterial oral rinse formulation of claim 1, wherein the antibacterial oral rinse formulation is contacted with an individual's oral cavity for a period of time ranging from between about 1 second to about 5 minutes immediately prior to said oral hygiene activity.

3. The antibacterial oral rinse formulation of claim 1, wherein the antibacterial oral rinse formulation is contacted with an individual's oral cavity for a period of time ranging from between about 10 seconds to about 3 minutes immediately prior to said oral hygiene activity.

4. The antibacterial oral rinse formulation of claim 1, wherein the antibacterial oral rinse formulation is contacted with an individual's oral cavity for a period of time ranging from between about 30 seconds to 60 seconds immediately prior to said oral hygiene activity.

5. The antibacterial oral rinse formulation of claim 1, wherein said contact comprises rinsing the inside of the mouth with between about 0.1 liquid ounce to about 10.0 liquid ounces of the antibacterial oral rinse formulation.

6. The antibacterial oral rinse formulation of claim 1, wherein said contact comprises rinsing the inside of the mouth with about 1.0 liquid ounce of the antibacterial oral rinse formulation.

7. The antibacterial oral rinse formulation of claim 1, wherein said oral hygiene activities are selected from the group consisting of tooth brushing and tooth flossing.

8. The antibacterial oral rinse formulation of claim 1, wherein said inflammatory diseases or inflammatory processes associated with diseases are selected from the group consisting of atherosclerotic plaque formation in coronary arteries, rheumatoid arthritis, lupus erythematosus and related disorders, osteoarthritis, inflammatory bowel disease, thyroiditis, chronic obstructive pulmonary disease, pericarditis, asthma, chronic fatigue syndrome, gout, kawasaki's disease, lymphadenopathy, polymyalgia rheumatica, psoriasis, raynaud's phenomenon, sarcoidosis, sjogren's syndrome, spondyloarthropathies and vasculitides.

9. The antibacterial oral rinse formulation of claim 8, wherein the inflammatory process associated with disease is atherosclerotic plaque formation in coronary arteries.

10. A method for inhibiting transient bacteremia associated with causing inflammatory diseases or inflammatory processes associated with diseases as a result of oral hygiene activities in an individual, comprising rinsing with the antibacterial oral rinse formulation of claim 1 for a period of time immediately prior to engaging in said oral hygiene activities.

11. A method for inhibiting bacterial growth on an oral hygiene device, comprising storing the oral hygiene device in the antibacterial oral rinse formulation of claim 1 between usage of the oral hygiene device.

12. The method according to claim 11, wherein the oral hygiene device is selected from the group consisting of manual toothbrushes, electrically-operated toothbrushes and dental floss.

13. The antibacterial oral rinse formulation of claim 8, wherein the oral rinse formulation further consists essentially of sweeteners selected from the group consisting of sorbitol, mannitol, aspartame, isomalt, saccharin, sucralose, alitame, maltitol, lactitol, xylitol and erythritol.

* * * * *